Figure 1:
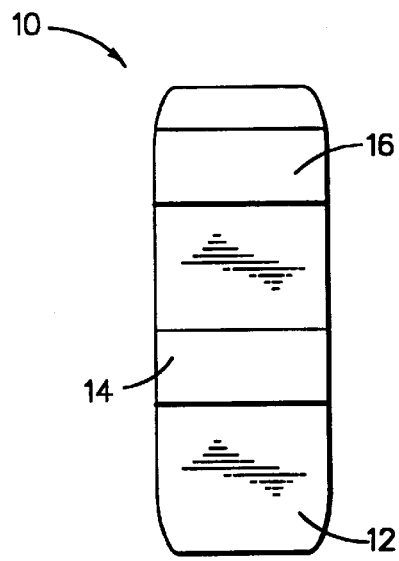

United States Patent [19]
Hatch et al.

[11] Patent Number: 6,033,918
[45] Date of Patent: Mar. 7, 2000

[54] METHOD AND DEVICE FOR THE DETECTION OF ANALYTE IN A FLUID SAMPLE

[75] Inventors: Robert P. Hatch; Meitak Teresa Yip, both of Elkhart, Ind.

[73] Assignee: Bayer Corporation, Elkhart, Ind.

[21] Appl. No.: 08/967,580

[22] Filed: Nov. 10, 1997

[51] Int. Cl.⁷ .................. G01N 33/548; G01N 33/553
[52] U.S. Cl. ................... 436/530; 436/525; 436/815
[58] Field of Search ................... 436/525, 530, 436/815

[56] References Cited

U.S. PATENT DOCUMENTS

| | | | |
|---|---|---|---|
| 4,908,405 | 3/1990 | Bayer et al. | 525/61 |
| 5,240,602 | 8/1993 | Hammen | 210/198 |
| 5,258,041 | 11/1993 | Guire et al. | 436/501 |
| 5,314,830 | 5/1994 | Anderson et al. | 436/524 |
| 5,403,928 | 4/1995 | Arrhenuis | 540/121 |
| 5,612,460 | 3/1997 | Zaplipsky | 530/391.9 |
| 5,736,344 | 4/1998 | Kung | 435/7.1 |
| 5,756,361 | 5/1998 | Winterbottom | 436/518 |
| 5,858,534 | 1/1999 | Sucholeiki | 428/407 |

FOREIGN PATENT DOCUMENTS

91/10141  7/1991  WIPO .

OTHER PUBLICATIONS

1979, Bodanszky, Active Esters in Peptide Synthesis.
Zaplisky et al, Polymer Preprints Am. Chem. Soc. Div. Polym. Chem., vol. 27, No. 1, pp. 1–2, 1986.
S. Zalipsky, Bioconjugate Chem., vol. 6, pp. 150–165. Functionalized Poly(ethylene glycol) for Preparation of Biologically Relevant Conjugates, 1995.

*Primary Examiner*—Mary E. Ceperley
*Attorney, Agent, or Firm*—Jerome L. Jefferson

[57] ABSTRACT

Disclosed is an improvement to the technique for immobilizing an analyte onto a solid surface for use in a competitive immunoassay. The improvement involves immobilizing the analyte on the solid surface by reacting the analyte or derivative thereof with polyethylene glycol which has been functionalized with a group which is reactive with the analyte contacting the resulting conjugate with the solid surface to thereby immobilize the analyte.

12 Claims, 1 Drawing Sheet

METHOD AND DEVICE FOR THE DETECTION OF ANALYTE IN A FLUID SAMPLE

BACKGROUND OF THE INVENTION

There is a need for simple diagnostic tests for common diseases that can be executed by untrained personnel. Simpler tests would allow for home or doctor's office testing when current procedures require the analysis to be done by an outside laboratory. Possible benefits of simpler tests are decreased turn-around time and a reduction in cost. Representative examples are home pregnancy and glucose testing.

A common format for these simpler tests is the immunostrip format. Usually this format contains a mobile phase consisting of the test solution and a labeled, analyte-specific antibody. The analyte binds to the antibody and passes through a capture zone which contains immobilized analyte or an analyte derivative which is immunologically reactive with the antibody. The capture zone removes excess labeled antibody as the bound labeled antibody migrates to a detection zone.

There are numerous analytes whose detection by such a diagnostic test could benefit the public. Accurate, stable and reproducible tests are highly desirable. By using the osteoporosis marker deoxypyridinoline, which is illustrative of analytes, it is the intent of this invention to describe polymer bound analytes that provide advantages when used to immobilize the analyte onto the immunostrip's capture zone.

Collagen is present in various forms in all tissue. It is now well accepted that collagen has the form of amino acid chains cross-linked by the pyridinium crosslinks pyridinoline (PYD) and deoxypyridinoline (DPD). The pyridinium crosslinks are formed from three hydroxylysine residues, two of which are from the terminal (non-helical) peptides of the collagen molecule that are enzymatically converted to aldehydes before reaction and a third hydroxylysine situated in the helical portion of a neighboring collagen molecule. There have been described techniques in the literature for the measurement of pyridinoline in urine by use of an enzyme labeled antibody specific to pyridinoline to form a pyridinoline enzyme labeled complex which can be detected by an enzyme-linked immunosorbant assay. While the analysis for PYD is useful as a means of screening for osteoporosis and rheumatoid arthritis, its presence in connective tissue, as well as in bone, can cause skewed results. Accordingly, immunoassays for deoxypyridinoline, which is only found in bone, have become preferred over those for PYD in the early detection of bone degradation.

Testing for DPD can be accomplished by contacting a fluid test sample, e.g. urine, with a labeled antibody specific for DPD. A particularly convenient method for DPD determination involves the use of a test strip of the type depicted in FIG. 1. Referring to FIG. 1, strip 10 having a labeled anti-DPD antibody complex (typically with gold sol as the labeling material) binds with DPD in the fluid test sample in application zone 12 of the strip 10. The labeled DPD antibody and DPD in the fluid test sample which is applied to the application zone 12 of the strip 10 form an immunocomplex which migrates due to capillary action through the capture zone of the strip 14 and the optional detection zone 16. In the capture zone 14, there is immobilized DPD which captures unbound, labeled anti-DPD. The signal generated by the label on the captured anti-DPD is measured, such as by means of a reflectance spectrophotometer, and correlated with the results of replicate strips used to assay fluid test samples containing known amounts of DPD. As in classical competitive immunoassays, the intensity of the signal generated in the capture zone will be inversely proportional to the concentration of the DPD in the fluid sample. Labeled anti-DPD, which is not captured in the capture zone 14 because it had combined with DPD in the fluid test sample, is captured in the detection zone 16 by anti-mouse IgG, specific for a different epitope on the anti-DPD antibody than the previously mentioned active binding site for DPD on the labeled anti-DPD, which is immobilized in this zone. By measuring the spectral response from the capture and detection zones, and analyzing this response using an appropriate algorithm, the accuracy of the assay can be increased.

Nitrocellulose, commonly used to bind proteins and poly (ethylene glycols), is a preferred material for use in preparing the type of test strip illustrated by FIG. 1. Polysulfones, nylons or other porous membranes capable of adsorbing macromolecules also provide suitable strip material. A common technique to immobilize an analyte onto nitrocellulose or other solid support is to covalently bind the analyte to a protein that irreversibly adsorbs onto the solid support. Applying the resulting conjugate to the solid support results in an irreversibly bound analyte.

To provide a quality product, sensitivity, stability and precision are highly desirable. The object of this invention is to provide conjugates which provide such sensitivity, stability and precision.

SUMMARY OF THE INVENTION

The present invention is an improvement to an immunoassay technique for an analyte in a fluid test medium in which a labeled antibody specific to the analyte is combined with the fluid test medium and the fluid test medium is then contacted with a solid support upon which the analyte or analyte derivative is immobilized. In this type of immunoassay, labeled antibody which has not reacted with the analyte in the test medium will react with and be bound by the immobilized analyte or derivative thereof. The improvement involves immobilizing the analyte or derivative onto the solid support using a conjugate prepared by reacting the analyte or derivative with polyethylene glycol functionalized on one or both ends with a group which is reactive for the analyte or derivative. When the polyethylene glycol is functionalized on only one end with the reactive group, it is functionalized on the other end with an unreactive capping group. The reactive group acts to bind the analyte or analyte derivative to the solid support.

DESCRIPTION OF THE INVENTION AND BRIEF DESCRIPTION OF THE DRAWINGS

A format in which the present invention can be carried out is illustrated by FIG. 1. For purposes of this discussion the analyte is DPD, but it is to be understood that other analyte are also detectable by using analogous systems. A gold sol anti-DPD antibody complex binds DPD in the fluid tests sample and migrates through the strip's zones. In the first zone, capture zone 14, immobilized DPD captures unbound gold sol/anti-DPD complex. The second zone, detection zone 16, containing goat anti-mouse IgG, captures the gold sol/anti-DPD that did not bind to DPD in the detection zone. The concentration of DPD in the fluid test sample can be determined by an algorithmic treatment of the reflectance measurements of the two zones. Capture zone 14 requires immobilized DPD. Bovine serum albumin (BSA) and polyethylene glycol (PEG) conjugates were prepared, optimized and immobilized on capture zone 14 of the nitrocellulose strip using the following technique:

Preparation of BSA-DPD conjugate: 1-(3-Dimethylaminopropyl)-3-ethyl carbodiimide (140 mg) was added to an ice cold solution consisting of 36 mg of bovine serum albumin (Bayer Pentex®, fraction V, protease free), 16 mg of sulfo N-hydroxysuccinimide and 3 mL of 100 mM, pH 8, EPPS. The solution was stirred 15 minutes at room temperature and cooled in an ice bath. The mixture was then added to a chilled solution of 4.4 mg of DPD in 6.28 mL of 10 mM HCl and allowed to stir for 4.5 hours in an ice bath. After 5° C. overnight storage, 26 mL of a 40 μM solution of lysine hydrochloride was added and the mixture stirred for 4 hours at room temperature. In a 50 mL Amicon stirred ultrafiltration unit, the reaction was concentrated and diluted four times with 50 mL of pH 7.4 PBS using a Amicon YM-30 membrane. The retentate was chromatographed on a 3×25 cm Sephadex G-25 column. Fractions 10–14 (6 mL fractions) contained the product as determined by UV monitoring. These were combined to provide a 1.2 mg/mL solution of BSA-DPD with an absorbance at 324 nm of 0.29 indicating a DPD to BSA ratio of 2.75. The PEG-DPD conjugate was prepared as described in the following Example IA.

Stability and precision data are presented in Table 1. A dose response curve for the PEG immobilized DPD is presented in FIG. 2.

TABLE 1

Comparison of Precision and Stability Between BSA and PEG Conjugates

| DPD Conjugate | Precision | | Stability at 40° C. % (Bias) | |
|---|---|---|---|---|
| | DPD (nM) | % CV(N=5) | 1 week | 4 week |
| BSA-DPD | 30 | 35.7 | −39% | −47% |
| | 100 | 12.1 | −10% | −16% |
| PEC-DPD | 30 | 0.6 | 11% | 13% |
| | 100 | 6.2 | −5% | 2% |

The data of Table 1 reveal that the PEG conjugates provide better precision and stability than the conjugates prepared using BSA as indicated by lower coefficients of variation and bias numbers. Better stability and precision indicate that the PEG conjugates are preferred in this formulation. Suitable for use in the present invention are polyethylene glycols of molecular weight greater than about 6,000. The preferred molecular weight is about 20,000 with a maximum molecular weight of about 35,000 being preferred. Polyethylene glycols with molecular weights up to 50,000 and greater may be used, however, the ability of the PEG conjugate to bind the analyte or analyte derivative drops off at these higher molecular weights.

The PEG is typically terminated at both ends with the analyte interactive functional group. It can, however, be terminated at one end with the functional group and on the other with an unreactive capping group such as an alkyl (preferably methyl) ether. Suitable reactive groups include activated carboxy, amino, epoxy, halo, sulfhydryl, isocyanate, maleimide and formyl.

When the analyte or derivative thereof bears one or more amino group, the reactive group on the polyethylene glycol can be epoxy, halo, isocyanate or activated carboxy due to the ability of these groups to form stable bonds with amines. Likewise, when the PEG is amine terminated and the analyte bears carboxyl groups, the binding between the PEG and the analyte is carried out using an activating agent such as thionyl chloride, N,N,N', N',-tetramethyl(succinimido) uronium tetrafluoroborate, isobutylchloroformate or N,N-dialkylcarbodiimide, in the presence of N-hydroxysuccinimide, p-nitrophenol, pentafluorophenol or pentachlorophenol.

When the reactive group on the PEG is formyl, it is combined with an amine bearing analyte or analyte derivative in the presence of a reducing agent to bind the analyte to the PEG through the amine. Suitable reducing agents include sodium cyanoborohydride and Pd/C with $H_2$.

In addition, the reactive group on the PEG can be a sulfhydryl when the analyte or derivative thereof bears a maleimide group or vice-versa so that the analyte is bound to the polymer via a 4-succinimide sulfide linkage.

Common methods of preparing analyte/polymer conjugates suitable for immobilizing the analyte to a solid support involve the reaction of proteins such as BSA with analytes in the presence of carbodiimides. In the case of amino acid bearing analytes, these reaction conditions cause the polymerization of the analyte through reaction of its amino and carboxylate groups. This problem can be circumvented by purifying the activated protein intermediate, however, this makes the procedure more time consuming due to the extra steps involved. The preactivated PEG reagents of the present invention react directly with the amino groups of amino acid bearing analytes to form conjugates without an intermediate purification step. Other advantages are that there is no polymerization of the analyte, this unreacted analyte can be recovered, and the reaction can be carried out under anhydrous conditions which allow a higher percentage of incorporation of the analyte into the polymer which is especially useful when the analyte is not readily available.

Figure 2:
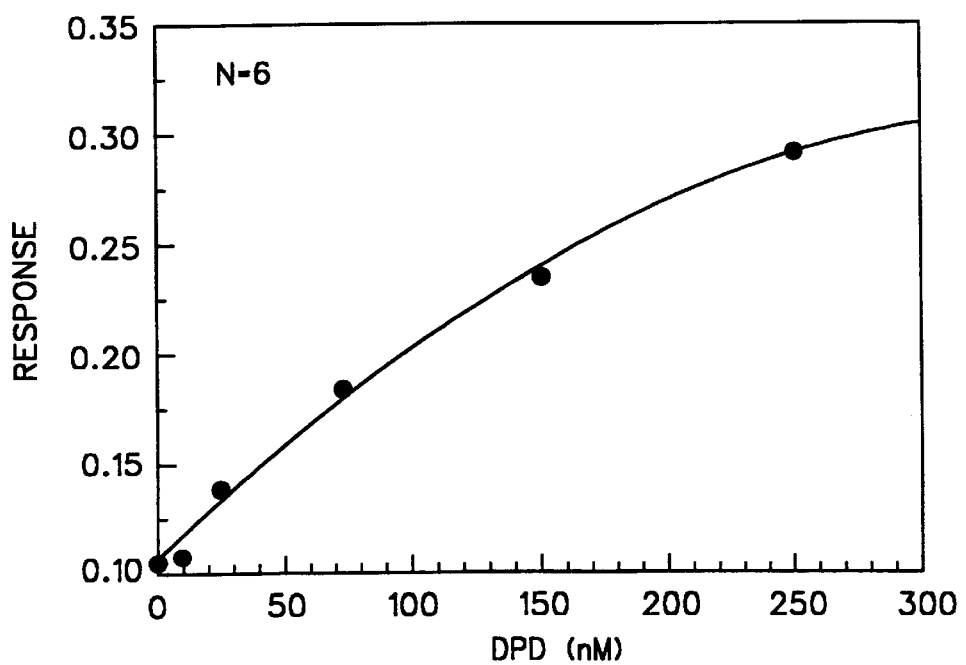

In early experiments, the PEG polymer used to form a conjugate with DPD had a molecular weight of 3400. Evaluation of this conjugate indicated that it bound a gold sol/anti-DPD complex in the presence of nitrocellulose but not in the presence of free DPD. From this it was concluded that either the conjugate did not bind the gold sol/anti-DPD conjugate tightly or the conjugate did not bind tightly to the nitrocellulose. As an alternative to the use of the 3400 molecular weight PEG, there was employed a higher molecular weight PEG (MW 20,000) which was found to absorb onto the nitrocellulose and bind unbound gold sol/DPD antibody conjugates. A dose response curve using 20,000 MW PEG-DPD conjugates in capture zone 14 is shown in FIG. 2.

The present invention is further illustrated by the following examples:

EXAMPLE I

Preparation of PEG-DPD Conjugates
A. Preparation of PEG(MW 20,000)-DPD Conjugate To 100 μL of 0.1 M, pH 8.0 4-(2-hydroxyethyl)-1-piperazine propane sulfonic acid (EPPS) was added 32 μL (0.198 μmole) of a 2.55 mg/mL solution of DPD which had been isolated from bone. Meanwhile, a 20 mg/mL solution of PEG(MW 20,000) bis N-hydroxysuccinnimidyl ester was prepared in dimethylformamide (DMF) and 100 μL (0.1 μmole) added to the DPD mixture. The reaction was allowed to stir at room temperature for 18 hours and was then purified by repeated (7x) concentration through a YM-3 membrane from Amicon followed by redilution with pH 7.4 (0.01 M) phosphate buffered saline (PBS) buffer. The retentate (1.86 mL) had an absorbance at 326 nm of 0.138. Assuming an 80% recovery of polymer, this absorption value indicates 0.7 DPD/PEG, i.e. an average of 0.7 DPD molecules bound to one PEG molecule.

B. Preparation of PEG(MW 50,000)-DPD Conjugate

A 40 μL sample of a 2.55 mg/mL solution of DPD was lyophilized and 200 μL of a solution comprising 0.54 μL/mL of triethylamine (0.784 μmole) in DMF was added to the residue. As a solid, 67.1 mg (0.12 μmole) of PEG (50,000) bis N-hydroxysuccinnimidyl ester was added and the mixture allowed to stir for 18 hours at room temperature. It was purified as described above except that a YM30 membrane from Amicon was used. The absorbance at 326 nm of a 1.6 mL solution of the retentate was 0.1 after compensation for the baseline. Assuming 80% recovery of the polymer, the DPD/PEG ratio was 0.38 The immobilization of DPD with the 50,000 MW PEG was not as effective as when lower molecular weight polymers were used, indicating the desirability of using lower molecular weight polymers.

EXAMPLE II

Preparation of the Reagent Pad

Reagents were deposited onto nitrocellulose membranes (16 cm×6 cm) in the following manner:

Two bands of anti-mouse IgG (1 mg/mL of PBS) were deposited onto the nitrocellulose at about 3 and 3.5 cm from the bottom of the membrane and at amounts of 2 μL/cm and 1 μL/cm respectively. Next three bands of PEG 20,000/DPD conjugate (0.85 mg/mL of PBS) were deposited on the same nitrocellulose membrane at about 1, 1.5 and 2 cm from its bottom in amounts of 2 μL/cm, 1 μL/cm and 1 μL/cm respectively. The nitrocellulose membrane was dried, blocked with casein solution (1% in PBS), washed with water and then dried at ambient conditions.

The nitrocellulose membrane was mounted on a polystyrene backing using an acrylic based adhesive. A gold sol/anti-DPD antibody pad 12 was then mounted at the position shown in FIG. 1 followed by the addition of an absorbant pad. This piece of the assembly was then slit into 4.2" (10.7 cm) by 0.2" (5.1 cm) strips.

For testing, the strips were dipped into a test tube containing the test solution, i.e. an aqueous solution containing various low molecular weight substances known to be present in urine as well as seven levels (0, 10, 25, 50, 75, 150 and 250 mM) DPD. After the liquid had reached the top of the nitrocellulose membrane, the strip was removed from the test tube and scanned for response with a CLINITEK® 50 reflectance spectrometer. The % reflectance at each of the five bands was measured and recorded. As shown in FIG. 2, a dose response curve was generated using the method of the present invention. This dose response curve illustrates that the technique of the present invention can successfully determine the concentration of DPD over the concentrations demonstrated.

The foregoing discussion has centered on deoxypyridinoline (DPD) as the analyte. However, the present invention is not limited to this particular analyte. Other small analytes, particularly those with molecular weights of less than about 1500, can be immobilized by the technique of the present invention. Examples of such analytes include digoxin, drugs of abuse such as thyroxine and anticonvulsant drugs such as phenylbarbitol, phenytoin and carbamazepine. The immobilization of DPD is particularly challenging because certain anti-DPD antibodies will not consistently recognize DPD immobilized by conventional BSA techniques. This lack of consistency is obviated by the present invention as illustrated by the data presented in Table 1.

We claim:

1. In an immunoassay for deoxypyridinoline (DPD) as analyte in a fluid test medium in which a labeled antibody specific to the DPD analyte is combined with the fluid test medium, which fluid test medium is then contacted with a solid support of nitrocellulose upon which the DPD analyte or analyte derivative is immobilized so that labeled antibody which has not reacted with the DPD analyte in the test medium will react and be bound by the immobilized DPD analyte or derivative thereof, the improvement which comprises immobilizing the DPD analyte or analyte derivative on the solid support using a conjugate prepared by reacting the DPD analyte or derivative thereof with polyethylene glycol having a molecular weight of greater than about 6,000 up to 50,000 functionalized on one or both ends with a group reactive with the DPD analyte or derivative thereof which reactive group is activated carboxy, amino, epoxy, halo, sulfhydryl, isocyanate maleimide or formyl and, when functionalized on only one end with a reactive group, the polyethylene glycol is functionalized on the other end with an unreactive capping group, wherein the reactive group acts to bind the DPD analyte or analyte derivative.

2. The immunoassay of claim 1 wherein the polyethylene glycol is functionalized on one end with an unreactive capping group which is an alkyl ether.

3. The immunoassay of claim 2 wherein the alkyl ether is methyl ether.

4. The immunoassay of claim 3 wherein the analyte or analyte derivative bears one or more amino group and the reactive group on the polyethylene glycol is epoxy, halo, isocyanate or activated carboxy.

5. The immunoassay of claim 4 wherein the reactive group is formyl and the analyte or derivative thereof is combined with the formyl substituted polyethylene glycol in the presence of a reducing agent.

6. The immunoassay of claim 5 wherein the reducing agent is sodium cyanoborohydride.

7. The immunoassay of claim 1 wherein the polyethylene glycol is substituted with amino groups, the analyte or analyte derivative bears carboxyl groups and the analyte is combined with the amino substituted polyethylene glycol by the reaction of its amino groups with the carboxyl groups on the analyte in the presence of an activating agent.

8. The immunoassay of claim 7 wherein the activating agent is thionyl chloride, N,N,N',N',-tetramethyl (succinimido) uronium tetrafluoroborate, isobutylchloroformate or N,N dialkylcarbodiimide used in the presence of N-hydroxysuccinimide, p-nitrophenol, pentafluorophenol or pentachlorophenol.

9. The immunoassay of claim 1 wherein the reactive group on the polyethylene glycol is a sulfhydryl and the analyte or analyte derivative contains a maleimide.

10. The immunoassay of claim 1 wherein the reactive group on the polyethylene glycol is a maleimide and the analyte or derivative thereof contains a sulfhydryl.

11. The immunoassay of claim 1 wherein the polyethylene glycol has a molecular weight of from about 20,000 to 35,000.

12. The immunoassay of claim 1 wherein the fluid test medium is urine.

* * * * *